United States Patent [19]

Lang et al.

[11] Patent Number: 4,775,526
[45] Date of Patent: Oct. 4, 1988

[54] 3-BENZYLIDENE BENZHETERAZOLES IN ULTRAVIOLET SCREENING COMPOSITIONS

[75] Inventors: Gerard Lang, Saint Gratien; Serge Forestier, Claye Souilly; Herve Richard, Paris, all of France

[73] Assignee: L'OREAL, Paris, France

[21] Appl. No.: 947,854

[22] Filed: Dec. 30, 1986

[30] Foreign Application Priority Data

Dec. 30, 1985 [FR] France ............... 85 19441

[51] Int. Cl.$^4$ ............ A61K 7/42; C07D 277/66; C07D 263/56; C07D 235/12
[52] U.S. Cl. ......................... 424/47; 424/59; 424/63; 8/405; 548/334; 548/224; 548/178
[58] Field of Search ........... 548/334, 178, 224; 424/59, 47, 63; 8/405

[56] References Cited

U.S. PATENT DOCUMENTS

| | | | |
|---|---|---|---|
| 3,781,417 | 12/1973 | Welters et al. | 424/59 |
| 3,786,046 | 1/1974 | Fumia et al. | 548/178 |
| 4,061,730 | 2/1977 | Bouillon et al. | 260/429.9 |
| 4,165,336 | 8/1979 | Bouillon et al. | 260/511 |
| 4,250,108 | 2/1981 | Bouillon et al. | 260/511 |
| 4,304,730 | 12/1981 | Kalopissis et al. | 424/59 |
| 4,323,549 | 4/1982 | Bouillon et al. | 424/45 |
| 4,327,031 | 4/1982 | Bouillon et al. | 260/429.9 |
| 4,330,488 | 5/1982 | Bouillon et al. | 260/511 |
| 4,421,739 | 12/1983 | Bouillon et al. | 424/47 |
| 4,588,839 | 5/1986 | Lang et al. | 564/84 |

Primary Examiner—John F. Terapane
Attorney, Agent, or Firm—Fleit, Jacobson, Cohn & Price

[57] ABSTRACT

A compound of formula:

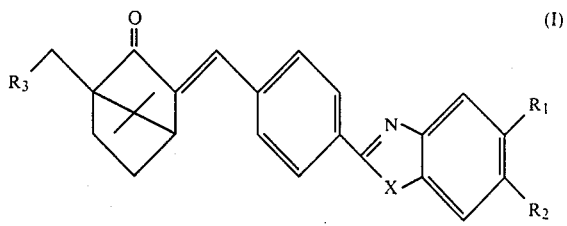

wherein:
x is oxygen, sulphur or an —NR—group, wherein R is hydrogen or a $C_1$-$C_6$ alkyl group;
$R_1$ is hydrogen or a $C_1$-$C_6$ alkyl, a $C_1$-$C_6$ alkoxy, an —$SO_2Cl$ or —$SO_2NR_4R_5$ group wherein $R_4$ and $R_5$, which may be identical or different, are hydrogen, a $C_1$-$C_{12}$ alkyl or $C_2$-$C_4$ hydroxyalkyl group, or $R_1$ is an —$SO_3H$ or —$SO_3^\ominus M^\oplus$ group wherein M is potassium or sodium or an $N(R_6)_4^\oplus$ group, wherein each $R_6$, which may be identical or different, is hydrogen, a $C_1$-$C_6$ alkyl or $C_2$-$C_4$ hydroxyalkyl group;
$R_2$ is hydrogen, a $C_1$-$C_6$ alkyl or $C_1$-$C_6$ alkoxy group, or $R_1$ and $R_2$ together are a methylenedioxy group;
$R_3$ is hydrogen or an —$SO_3H$, —$SO_3^\ominus M^\oplus$ or —$SO_2NR_4R_5$ group wherein M, $R_4$ and $R_5$, which may be the identical or different to the M, $R_4$ and $R_5$ groups respectively above, have the same meanings as above is useful in cosmetics for protection against ultra-violet rays.

20 Claims, No Drawings

3-BENZYLIDENE BENZHETERAZOLES IN ULTRAVIOLET SCREENING COMPOSITIONS

The present invention relates to 3-benzylidenecamphor compounds containing a benzimidazole, benzoxazole or benzothiazole group, a process for preparing them and to their use in the cosmetic field for protection against ultraviolet radiation.

It is known that light radiation of wavelengths from 280 to 400 nm darken the human epidermis, and that radiation of wavelengths from 280 to 320 nm, known as UV-B, also induce erythema and cutaneous burns which can impair the development of the tan.

Compounds which absorb radiation in the wavelength range of from 280 to 320 nm are already known.

Nevertheless, while UV-B rays are known to have an essential role in the production of solar erythema, and are therefore desirably filtered out, UV-A rays of wavelengths from 320 400 nm, which induce darkening of the skin, also induce deterioration of the skin, especially in the case of sensitive skin or skin exposed continuously to solar radiation, and speed up the ageing of the skin. It has been found that UV-A rays can enhance the action of UV-B rays; see, for example, J. WILLIS, A. KLIGMAN and J. EPSTEIN, The Journal of Investigative Dermatology, Vol. 59, No. 6, page 416, 1973, who refer to "photo augmentation". UV-A rays promote the initiation of the erythematous reaction or magnify this reaction in some subjects. Likewise, they can be at the source of phototoxic or photoallergic reactions.

It is also desirable to protect the hair from photochemical degradation, so as to avoid a change in shade, bleaching or degradation of its mechanical properties.

It is known that constituents which may be included in cosmetic preparations, especially certain dyes in dyeing compositions, colored hair lacquer, shampoos, hair setting lotions, and make-up products such as tinted creams, nail varnishes and lipsticks, do not always possess sufficient stability to light, and that they can be degraded through the action of light radiation.

In consequence, it is desirable to have compounds capable of absorbing UV-A rays and having a high absorbing power enabling them to be used at low concentrations in formulations, especially in cosmetic compositions intended for application on the human epidermis.

We have discovered that certain 3-benzylidenecamphor compounds containing a benzimidazole, benzoxazole or benzothiazole group surprisingly possess good UV-A filtering properties and also possess good photochemical stability.

Accordingly the present invention provides a compound of formula:

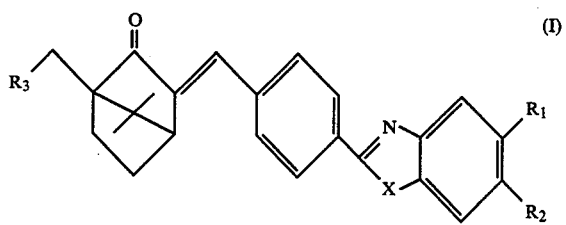

(I)

wherein:

X is oxygen, sulphur or an —NR— group, wherein R is hydrogen or $C_1$–$C_6$ alkyl group;

$R_1$ is hydrogen or a $C_1$–$C_6$ alkyl, a $C_1$–$C_6$ alkoxy, an —SO$_2$Cl or —SO$_2$NR$_4$R$_5$ group wherein R$_4$ and R$_5$, which may be identical or different, are hydrogen, a $C_1$–$C_{12}$ alkyl or $C_2$–$C_4$ hydroxyalkyl group, or $R_1$ is an —SO$_3$H or —SO$_3^\ominus$M$^\oplus$ group wherein M is potassium or sodium or an N(R$_6$)$^\oplus_4$ group, wherein each R$_6$, which may be identical or different, is hydrogen, a $C_1$–$C_6$ alkyl or $C_2$–$C_4$ hydroxyalkyl group;

$R_2$ is hydrogen, a $C_1$–$C_6$ alkyl or $C_1$–$C_6$ alkoxy group, or $R_1$ and $R_2$ together are a methylenedioxy group;

$R_3$ is hydrogen or an —SO$_3$H, —SO$_3^\ominus$M$^\oplus$ or —SO$_2$NR$_4$R$_5$ group wherein M, R$_4$ and R$_5$, which may be the identical or different to the M, R$_4$ and R$_5$ groups respectively above, have the same meanings as above.

The alkyl groups may be linear or branched. Examples of $C_1$–$C_6$ alkyl groups are methyl, ethyl, n-propyl, isopropyl, n-butyl, sec-butyl and tert-butyl groups. Examples of alkoxy groups are methoxy, ethoxy, n-propoxy and n-butoxy groups. Examples of $C_1$–$C_{12}$ alkyl groups include those mentioned above for the $C_1$–$C_6$ alkyl groups and hexyl and 2-ethylhexyl groups.

Depending on the nature of the $R_1$ and/or $R_3$ groups the compounds of formula I can be water-soluble or lipid soluble.

If $R_1$ and/or $R_3$ are an —SO$_3^\ominus$M$^\oplus$ group wherein M is sodium, potassium or an ammonium or substituted ammonium group, the compounds according to the present invention are water soluble. In all other cases, they are soluble in oils or fats.

The compounds of formula I according to the invention have high molar absorption coefficients ($\epsilon$), generally greater than 30,000 and often more than 40,000 at a wavelength of from approximately 320 to 350 nm.

The present invention also provides a process for preparing a compound of formula I.

If $R_3$ is hydrogen, the process comprises, in a first stage, reacting 3-(4-formylbenzylidene)-2-bornanone and an ortho-phenylenediamine unsubstituted or substituted on one nitrogen atom and/or on the aromatic ring, or a 2-aminophenol or 2-aminothiophenol unsubstituted or substituted on the aromatic ring in a non-oxidizing medium, comprising an inert atmosphere and a $C_1$–$C_4$ alcohol or aromatic hydrocarbon solvent at a temperature from room temperature to the refluxing temperature of the reaction mixture to form a Schiff's base and, in a second stage, oxidative cyclizing the Schiff's base thereby formed to obtain the compound of formula I.

Examples of preferred aromatic hydrocarbons are toluene and xylene.

The oxidative cyclization is generally performed using benzoyl peroxide, N-bromosuccinimide, activated manganese dioxide, barium manganate or lead tetraacetate, but more advantageously under reflux in toluene in the presence of a catalytic amount of ferric chloride and with air bubbled through for ortho-phenylenediamines, or under reflux in xylene in the presence of chloranil and with air bubbled through for 2-aminophenols and 2-aminothiophenols.

The compounds of formula (I) in which $R_1$ is an —SO$_2$Cl group may be obtained by chlorosulphonation of the corresponding compound of formula (I) in which $R_1$ is hydrogen. The chlorosulphonation is generally performed at a temperature below or equal to 30° C., in the presence of an excess of chlorosulphonic acid and optionally in a chlorinated solvent.

By alkaline hydrolysis with sodium carbonate or potassium carbonate of the chlorosulphonic derivative under reflux it is possible to obtain a compound of formula (I) in which $R_1$ is an $-SO_3^{\ominus}M^{\oplus}$ group in which M is sodium or potassium.

By exchanging the alkali metal ion present in the alkali metal sulphonate derivative, for example by ion exchange, the free sulphonic acid can be prepared. By neutralizing the free sulphonic acid with an equivalent amount of an amine or ammonia, it is possible to obtain a compound of formula (I) in which $R_1$ is an $-SO_3^{\ominus}M^{\oplus}$ group in which M is an ammonium or substituted ammonium group.

Compounds of formula (I) in which X is an $-NR-$ group, wherein R is a linear or branched $C_1-C_6$ alkyl group, may be obtained by alkylation of the corresponding compound of formula (I) in which X is an $-NH-$ group, generally using an alkyl iodide or a dialkyl sulphate in the presence of a base. The N-methyl derivative is more advantageously obtained by using dimethylformamide dimethyl acetal.

The compound of formula (I) in which $R_3$ is an $SO_3H$ group can be obtained by condensing 3-(4-carboxybenzylidene)-10-camphorsulphonic acid with an orthophenylenediamine unsubstituted or substituted on one nitrogen atom and/or on the aromatic ring, or with a 2-amihophenol or 2-aminothiophenol unsubstituted or substituted on the aromatic ring, in polyphosphoric acid or boric acid.

The compounds of formula (I) in which $R_1$ and/or $R_3$ are $-SO_2NR_4R_5$ groups can be obtained from the corresponding chlorosulphonic compound by reacting it with ammonia, a primary or secondary alkylamine, or a primary or secondary hydroxyalkylamine.

The present invention also provides a cosmetic composition comprising, as a protective agent against ultraviolet rays, an effective amount of at least one 3-benzylidenecamphor derivative of formula (I) in a cosmetically acceptable medium.

The composition, when used as a composition intended to protect the epidermis against ultraviolet rays, can be in any form customarily used for this type of composition. In particular, it may be a solution, a lotion, an emulsion such as a cream or milk, a gel or a solid stick, or is packaged as an aerosol.

It can contain the cosmetic adjuvants customarily used in this type of composition, such as thickeners, demulcents, humectants, emollients, wetting agents, surfactants, preservatives, antifoams, perfumes, oils, waxes, colorings and/or pigments whose function is to color the composition itself or the skin, bactericides or any other ingredient customarily used in cosmetics.

The compound of formula (I) is preferably present in a porportion of from 0.5 to 10% by weight, preferably from 1 to 6% by weight, relative to the total weight of the composition.

A solubilization solvent, such as a $C_1-C_6$ monohydric alcohol or polyol, a glycol or a glycol ether, an oil, a wax or a mixture thereof, or a hydroalcoholic solution, may be used. Especially preferred monohydric alcohols or polyols are ethanol, isopropanol and glycerin. Especially preferred glycols or glycol ethers are 2-butoxyethanol, ethylene glycol, ethylene glycol monoethyl ether, propylene glycol, diethylene glycol monoethyl ether and monomethyl ether, propylene glycol monomethyl ether and tripropylene glycol monomethyl ether and mixtures thereof.

One embodiment of the invention is an emulsion in the form of a protective cream or milk comprising, in addition to the compound of formula (I), fatty alcohols, fatty acid esters and, in particular, fatty acid triglycerides, fatty acids, lanolin, natural or synthetic oils, or waxes and water and an emulsifier.

Another embodiment consists of lotions such as oil-and-alcohol-based lotions, based on $C_1-C_6$ alcohols such as ethanol or a glycol such as propylene glycol and/or a polyol such as glycerin, and fatty acid esters such as fatty acid triglycerides.

The cosmetic composition of the invention can also be a hydroalcoholic or oil-and-alcohol-based gel comprising one or more $C_1-C_6$ alcohols such as ethanol, propylene glycol or glycerin, and a thickener, in the presence of water or oil, respectively.

The present invention also provides a cosmetic composition for protection against sunlight comprising at least one compound of formula (I) and at least one other sunscreen agent specific for UV-B radiation and compatible with the compounds of the invention. It is thus possible to obtain a formulation which filters out both UV-B and UV-A radiation.

The compositions according to the invention may therefore comprise a UV-B screening agent such as a lipid-soluble compound or an oil having screening properties, such as coffee oil. Examples of lipophilic UV-B sunscreen agents are salicylic acid derivatives such as 2-ethylhexyl salicylate and homomenthyl salicylate, cinnamic acid derivatives such as 2-ethylhexyl p-methoxycinnamate and 2-ethoxyethyl p-methoxycinnamate, p-aminobenzoic acid derivatives such as amyl p-(dimethylamino)benzoate and 2-ethylhexyl p-(dimethylamino)benzoate, benzophenone derivatives such as 2-hydroxy-4-methoxybenzophenone and 2,2'-dihydroxy-4-methoxybenzophenone, camphor derivatives such as 3-benzylidenecamphor, 3-(4-methylbenzylidene)camphor, the parasubstituted 3-benzylidenecamphors described in French Pat. Nos. 2,383,904, 2,402,647 and 2,421,878, and the sulphonamides derived from 3-benzylidenecamphor described in French Pat. No. 2,529,887, and more especially N-(2-ethylhexyl)-4-(3-methylidenecamphor) benzenesulphonamide and N-(2-ethylhexyl)-3-benzylidene-10-camphorsulphonamide.

Further examples of water-soluble sunscreen agents which filter out UV-B rays and are also capable of being combined with the lipid-soluble or water-soluble screening agents according to the invention provided they are compatible with these latter, include the benzylidenecamphor derivatives described in French Pat. Nos. 2,199,971, 2,236,515 and 2,282,426, and more especially 4-[(2-oxo-3bornylidehe)methyl]phenyltrimethylammonium methylsulphate and the salts of 4-[(2-oxo-3-bornylidene)methyl]benzenesulphonic acid and of 2-methyl-5-[(2-oxo-3-bornylidene)methyl]benzenesulphonic acid, as well as salts of 2-phenylbenzimidazole-5-sulphonic acid.

The composition protecting against sunlight according to the invention can take the form of, for example, solutions, lotions, emulsions such as a cream or milk, oils, fatty gels, or hydroalcoholic or oil-and-alcohol-based gels, or can be packaged as an aerosol or as solid sticks. They may contain the abovementioned cosmetic adjuvants customarily used in this type of composition.

The compositions may be hair care compositions such as hair lacquers, setting lotions, optionally having treatment or disentangling properties, shampoos, coloring shampoos, hair dyeing compositions, make-up products such as nail varnishes, treatment creams for the epidermis, make-up foundations and lipsticks, or any other cosmetic composition which may be unstable to light during storage as a result of its constituents.

The present invention also provides compositions intended to protect natural or sensitized hair against UV rays. These compositions generally take the form of shampoos, lotions, gels or emulsions to be rinsed and for application before or after shampooing, before or after dyeing or bleaching, before or after permanent waving, styling or treatment lotions, lotions for blow-drying or setting, hair lacquers, and compositions for permanent waving, dyeing or bleaching the hair. These compositions may contain, in addition to the compound of formula (I), various adjuvants customarily used in this type of composition, such as surfactants, thickeners, polymers, demulcents, preservatives, foam stabilizers, electrolytes, organic solvents, silicone derivatives, oils, waves, grease-removal agents, colorings and/or pigments whose function is to color the composition itself or the hair, and any other ingredient customarily used in the hair care field.

When the compositions form shampoos, they preferably also contain at least one anionic, nonionic or amphoteric surfactant, or a mixture thereof and the compound of formula (I) in an aqueous medium. The shampoos can also contain different adjuvants such as cationic surfactants, colorings, preservatives, thickening agents, foam stabilizing agents, synergists, demulcents, electrolytes, sequestering agents, one or more cosmetic resins, perfumes, natural substances and oils, as well as any other adjuvant used in a shampoo. In these shampoos, the concentration of surfactant is generally from 2 to 50% by weight.

When the compositions form non-rinsed lotions (lotions for blow-drying, setting lotions, styling or treatment lotions) they preferably comprise, generally in aqueous, alcoholic or hydroalcoholic solution, in addition to the compound of formula (I), at least one cationic, anionic, nonionic or amphoteric polymer, or a mixture thereof, in an amount generally of from 0.1 to 10%, preferably from 0.1 to 3%, by weight, and optionally antifoaming agents.

When the compositions form rinsed lotions, also known rinses, they are applied before or after bleaching, before or after permanent waving, before or after shampooing or between two stages of shampooing, and are then rinsed after an exposure time.

These compositions can be aqueous or hydroalcoholic solutions optionally comprising surfactants, emulsions or gels. These compositions can also be pressurized as an aerosol.

The surfactants which can be used in the solutions are mainly nonionic or cationic surfactants. The concentration of surfactants preferably is from 0.1 to 10% by weight, and is preferably from 0.5 to 7% by weight.

Nonionic, cationic, anionic or amphoteric polymers can be added to these compositions, and optionally anionic or amphoteric surfactants.

When the compositions take the form of an emulsion, they can be nonionic or anionic. The nonionic emulsions consist principally of a mixture of oils and/or fatty alcohols and polyethoxylated fatty alcohols, such as polyethoxylated stearyl or cetyl/stearyl alcohols, in the presence of water. Cationic surfactants or cationic polymers can be added to these emulsions.

The anionic emulsions are formed from soaps and contain the compound or compounds of formula (I) of an anionic or nonionic nature.

When the compositions take the form of gels, they contain thickeners and optionally a solvent. Examples of such thickeners are sodium alginate, gum arabic, xanthan gum or cellulose derivatives such as methylcellulose, hydroxymethylcellulose, hydroxyethycellulose, hydroxypropylcellulose and hydroxypropylmethylcellulose. Thickening of the lotions can also be obtained by a mixture of polyethylene glycol and polyethylene glycol stearate or distearate, or by a mixture of phosphoric esters and amides. The concentration of thickeners is preferably from 0.1 to 30%, and more preferably from 0.5 to 15%, by weight.

The present invention also provides a process for protecting the skin and natural or sensitized hair against UV-A rays, which consists in applying on the skin or hair an effective amount of at least one compound of formula (I) contained in a cosmetically acceptable medium or a composition containing the compound of formula (I).

The present invention also provides a process for protecting a colored cosmetic composition against UV-A rays, which consists in incorporating an effective amount of at least one compound of formula (1) in the composition.

The present invention will now be further described by means of the following Examples in which the melting point, wavelength corresponding to the absorption maximum ($\lambda_{max}$) and molar absorption coefficient ($\epsilon$) of the compounds of formula (I) of Examples 1 to 8 are shown in the table below:

TABLE I

| Ex. No. | Compound | Melting point | UV absorption in ethanol $\lambda_{max}$ (nm) | ($\epsilon$) |
|---|---|---|---|---|
| 1 | 3-[4-(Benzimidazol-2-yl)-benzylidene]-2-bornanone | 278° C. | 342 | 39700 |
| 2 | 3-[4-(Benzoxazol-2-yl)-benzylidene]-2-bornanone | 180° C. | 337 | 39500 |
| 3 | 3-[4-(Benzothiazol-2-yl)-benzylidene]-2-bornanone | 170–171° C. | 343 | 38380 |
| 4 | 3-[4-(5-Ethylbenzoxazol-2-yl)benzylidene]-2-bornanone | 199–200° C. | 339 | 44800 |
| 5 | 3-[4-(5-Methylbenzimidazol-2-yl)benzylidene]-2-bornanone | 158–160° C. | 347 | 36400 |
| 6 | 3-[4-(5-Methoxybenzimidazol-2-yl)benzylidene]-2-bornanone | 255° C. | 351 | 31000 |
| 7 | 3-[4-(5-Sulphobenzimidazol-2-yl)benzylidene]-2-bornanone potassium salt | >280° C. | 343 | 44260 |
| 8 | 3-[4-(N—Methylbenzimidazol-2-yl)benzylidene]-2-bornanone | 155° C. | 320 | 32800 |

The NMR spectra of these compounds are in agreement with these structures stated.

PREPARATION EXAMPLES

EXAMPLE

Preparation of the compound No. 1 of the Table 3-[4-(Benzimidazol-2-yl)benzylidene]-2-bornanone An ethanolic solution (500 ml) of 3-(4-formylbenzylidene)-2-bornanone (81.8 g; 0.305 mole) and ortho-phenylenediamine (33 g; 0.305 mole) is heated to the refluxing temperature for 1 hour under nitrogen while the mixture is stirred. An orange-yellow solid is formed in the medium. The reaction mixture is cooled in ice and the solution filtered to give the Schiff's base (93 g; 85% yield): orange-yellow solid, melting point 146° C.

This solid is dissolved in dry toluene (2.5 l) and heated for 8 hours at 80°–90° C. with 0.82 g of ferric chloride, air being bubbled through the solution. After the mixture has returned to room temperature, a pale brown precipitate is collected. After recrystallization in isopropanol with treatment with animal charcoal, and filtration hot on celite, the benzimidazole No. 1 is obtained (51 g; 55% yield): pale beige powder; mass spectrum (70 eV): for $C_{24}H_{24}N_2O$: $M+356$ (100%).

Elementary analysis:

|  | Elementary analysis: | | |
| --- | --- | --- | --- |
|  | C % | H % | N % |
| Calculated | 80.86 | 6.79 | 7.86 |
| Found | 80.83 | 6.86 | 7.81 |

EXAMPLE 2

Preparation of the compound No. 2 of the Table 3-[4-(Benzoxazol-2-yl)benzylidene]-2-bornanone An ethanolic solution (300 ml) of 2-aminophenol (9.62 g; 0.088 mole) and 3-(4-formylbenzylidene)-2-bornanone (23.7 g; 0.088 mole) is heated to reflux under nitrogen for 2 hours. The Schiff's base (20.6 g; 65% yield) is collected by filtration: pale yellow solid, melting point 175° C.

This solid is dissolved in 500 ml of xylene and heated to 120° C. while air is bubbled through and in the presence of chloranil (14.1 g) for 4 hours. After the mixture is cooled, the solvent is removed under reduced pressure and the residue is taken up in toluene. After chromatography on a silica column (eluent: $CH_2Cl_2/AcOEt$, 95:5), the benzoxazole No2 is obtained (16 g; 78% yield): pale yellow solid.

Elementary analysis

|  | Elementary analysis: | | |
| --- | --- | --- | --- |
|  | C % | H % | N % |
| Calculated | 80.64 | 6.49 | 3.92 |
| Found | 80.67 | 6.52 | 3.89 |

EXAMPLE 3

Preparation of the compound No. 3 of the Table 3-[4-(Benzothiazol-2-yl)benzylidene]-2-bornanone As for the previous example, 2-aminothiophenol (9.94 ml; 0.13 mole) and 3-(4-formylbenzylidene)-2-bornanone (35 g; 0.13 mole) are solubilized in the hot state under nitrogen in 500 ml of ethanol. After 2 hours under reflux, cooling of the reaction mixture and filtration, the Schiff's base is obtained (46 g; 95% yield): orange-yellow solid, melting point 92°–98° C.

This solid (38 g; 0.101 mole) is dissolved in 500 ml of xylene and heated to 120° C. while air is bubbled through, with 30 g of chloranil, for 4 hours. After evaporation of the solvent, a red-brown gum is obtained which is recrystallized in isopropanol to give the benzothiazole No. 3 (17.1 g; 45% yield): white crystals.

Elementary analysis:

|  | Elementary analysis: | | | |
| --- | --- | --- | --- | --- |
|  | C % | H % | N % | S % |
| Calculated | 77.17 | 6.21 | 3.75 | 8.58 |
| Found | 77.21 | 6.32 | 3.82 | 8.46 |

EXAMPLE 4

Preparation of the compound No. 4 of the Table 3-[4-(5-Ethylbenzoxazol-2-yl)benzylidene]-2-bornanone According to the same procedure as Example 2, with 2-amino-4-ethylphenol (6.1 g; 0.023 mole), the corresponding Schiff's base is obtained (8.0 g; 91% yield): pale yellow crystals, melting point 178°–9° C.

The latter compound, treated in the same manner as in Example 2, gives the crude benzoxazole (6.5 g; 85% yield). The chromatography stage was replaced by recrystallization in isopropanol, to give the benzoxazole No. 4 (3.7 g; 57% yield): pale yellow crystals.

Elementary analysis:

|  | Elementary analysis: | | |
| --- | --- | --- | --- |
|  | C % | H % | N % |
| Calculated | 81.01 | 7.06 | 3.63 |
| Found | 80.60 | 6.98 | 3.51 |

EXAMPLE 5

Preparation of the compound No. 5 of the Table 3-[4-(5-Methylbenzimidazol-2-yl)benzylidene]-2-bornanone The procedure is the same as that in Example 1, starting with 4-methyl-ortho-phenylenediamine (17.2 g; 0.136 mole) and 3-(4-formylbenzylidene)-2-bornanone (36.6 g; 0.136 mole) in 250 ml of ethanol. After 2 hours' refluxing while nitrogen is bubbled through, a blood-red solution is obtained which is concentrated almost to dryness. The oil obtained is solubilized in 50 ml of toluene, and the solution is poured into 2 litres of hexane with stirring to obtain an orange precipitate of the Schiff's base (22.8 g; 46% yield), melting point 128°–130° C.

This solid (18 g; 0.048 mole) was treated under the conditions of Example 1 to give a grey powder (15.1 g; 85% yield), which was purified on a silica bed in toluene and recrystallized in ethanol/water (2:1). After being dried under vacuum, the benzimidazole No. 5 is obtained (7.5 g; 42% yield).

Elementary analysis:

|  | Elementary analysis: | | |
| --- | --- | --- | --- |
|  | C % | H % | N % |
| Calculated | 81.05 | 7.07 | 7.56 |
| Found | 80.66 | 7.19 | 7.43 |

EXAMPLE 6

Preparation of the compound No. 6 of the Table 3-[4-(5-Methoxybenzimidazol-2-yl)benzylidene]-2-bornanone As in the previous example, with 4-methoxy-ortho-phenylenediamine (23.7 g; 0.135 mole) the corresponding Schiff's base is obtained (22.4 g; 45% yield): yellow solid, melting point 138°–142° C.

The Schiff's base (22 g; 0.0594 mole) was brought to 85°–90° C. in dry toluene for 6 hours with 0.5 g of ferric chloride and while air was bubbled through. After cooling of the solution and filtration, a pasty solid (17 g) was obtained, which was recrystallized twice in an ethyl acetate/ethanol (95:5) mixture to give the benzimidazole No. 6 (12.8 g; 55% yield): pale beige powder.

Elementary analysis:

|  | C % | H % | N % |
|---|---|---|---|
| Calculated | 77.69 | 6.78 | 7.25 |
| Found | 77.57 | 6.53 | 6.89 |

EXAMPLE 7

Preparation of the compound No. 7 of the Table 1st stage: Preparation of 3-[4-(5-chlorosulphonylbenzimidazol-2-yl)benzylidene]-2-bornanone In a 250-ml round-bottomed flask equipped with a condenser and a calcium chloride guard tube, the derivative No. 1 (20 g; 0.056 mole) is added portionwise in the course of 1 hour to 98% strength chlorosulphonic acid (131 g) cooled to +5° C. in a bath of ice-cold water. The mixture is left stirred at room temperature overnight. The black liquid obtained is allowed to flow dropwise in the course of 1 hour and with stirring into 3 kg of ice-cold water, without the temperature exceeding 10° C. The mixture is filtered and the precipitate washed with water. It is dried over $P_2O_5$ under vacuum, and 24.5 g of pale beige powder are obtained.

2nd stage: Preparation of 3-[4-(5-sulphobenzimidazol-2-yl)benzylidene]-2-bornanone potassium salt A suspension of the compound obtained in the 1st stage (15.9 g; 0.0356 mole) in saturated potassium carbonate solution (1.1 kg) is brought to reflux for 5 hours. The mixture is allowed to cool to 40° C. and is filtered on sintered glass No. 4. After being dried for 24 hours over $P_2O_5$ under vacuum, the derivative No. 8 is obtained (12.6 g; 73% yield): pale beige powder.

By acidification of an aqueous solution of the derivative No. 8, the corresponding sulphonic acid is obtained after filtration, washing with water and drying over $P_2O_5$ under vacuum: white powder.

Elementary analysis:
Calculated for $C_{24}H_{24}N_2O_4S \cdot H_2O$

|  | C % | H % | N % | S % |
|---|---|---|---|---|
| Calculated | 63.42 | 5.77 | 6.16 | 7.05 |
| Found | 63.60 | 5.58 | 6.03 | 6.69 |

EXAMPLE 8

Preparation of the compound No. 8 of the Table 3-[4-(N-Methylbenzimidazol-2-yl)benzylidene]-2-bornanone The derivative No. 1 (4.7 g; 0.013 mole) in 80 ml of dry toluene was heated under reflux for 12 hours with dimethylformamide dimethyl acetal (6.8 g; 0.056 mole). The solution was concentrated under vacuum and the red oil obtained chromatographed on a silica column (eluent: $CH_2Cl_2$/AcOEt, 9:1). The N-methylbenzimidazole 9 was obtained (3.4 g; 70% yield): fractured white solid.

Elementary analysis:

|  | C % | H % | N % |
|---|---|---|---|
| Calculated | 81.05 | 7.07 | 7.56 |
| Found | 80.68 | 7.06 | 7.62 |

APPLICATION EXAMPLES

Compositions for protection of the skin

EXAMPLE 9

| Oil-in-water emulsion | |
|---|---|
| Compound of Example 3 | 2 g |
| 50:50 mixture of glycerol monostearate and polyethylene glycol stearate containing 100 moles of ethylene oxide | 8 g |
| Stearyl alcohol | 6 g |
| Benzoate of $C_{12}$–$C_{15}$ alcohols, sold under the name "FINSOLV TN" by FINETEX | 30 g |
| Polydimethylsiloxane sold under the name "DOW CORNING FLUID 200" by DOW CORNING | 1 g |
| Tert-butyl-para-cresol | 0.05 g |
| Glycerin | 20 g |
| Ethylenediaminetetraacetic acid potassium salt dihydrate | 0.1 g |
| Preservative | 0.2 g |
| Perfume | 0.2 g |
| Demineralized water q.s. | 100 g |

The fats are heated to about 80°–85° C.; the screening agent of formula (I) is added. Separately, the water containing the water-soluble compounds is heated to 80°–85° C., and the fatty phase is added to the aqueous phase. After 15 minutes, brisk agitation, the mixture is allowed to cool with moderate agitation.

EXAMPLE 10

| Oil |  |
|---|---|
| The following ingredients are mixed, heating, if required, to 40–45° C. to homogenize: | |
| Compound of Example 2 | 1.5 g |
| Tripropylene glycol monomethyl ether | 70 g |
| Pentaerythritol tetracaprylate/caprate sold by CRODA under the name "CRODAMOL PTC" | 15 g |
| Sesame oil | 13.5 g |

EXAMPLE 11

| Oil-in-water emulsion | |
|---|---|
| Compound of Example 5 | 2 g |
| Glycerin | 20 g |
| Cetyl alcohol | 4 g |
| Mixture of cetyl/stearyl alcohol and sodium lauryl sulphate (90:10) | 6 g |
| Tert-butyl-para-cresol | 0.05 g |
| Polydimethylsiloxane sold under the name "DOW CORNING FLUID 200" by DOW CORNING | 1 g |
| Polyoxyethylenated glycerol monolaurate containing 8 moles of ethylene oxide, sold by CRODA under the name "GLYCEROX L8" | 20 g |
| Ethylenediamine tetraacetic acid potassium salt dihydrate | 0.1 g |
| Preservative | 0.2 g |
| Perfume | 0.2 g |

-continued

| Oil-in-water emulsion | |
|---|---|
| Demineralized water q.s. | 100 g |

This emulsion is prepared in the same manner as in Example 10.

EXAMPLE 12

| Oil |
|---|
| The following ingredients are mixed, heating, if required, to 40–45° C. to homogenize: |

| | |
|---|---|
| Compound of Example 1 | 1 g |
| Stearyl benzoate | 20 g |
| Propylene glycol monomethyl ether | 14 g |
| Tripropylene glycol monomethyl ether | 64.5 g |
| Perfume | 0.5 g |

EXAMPLE 13

| Oil |
|---|
| The following ingredients are mixed, heating, if required to 40–45° C. to homogenize: |

| | |
|---|---|
| Compound of Example 7 | 2 g |
| Propylene glycol | 50 g |
| Tert-butylhydroquinone | 0.02 g |
| Perfume | 0.4 g |
| Oleyl alcohol q.s. | 100 g |

EXAMPLE 14

| Gel | |
|---|---|
| Compound of Example 7 | 1 g |
| Propylene glycol | 50 g |
| Glycerin | 10 g |
| Preservative | 0.2 g |
| Xanthan gum sold under the name KELTROL by KELCO | 1 g |
| Water q.s. | 100 g |

EXAMPLE 15

| Oil-in-water emulsion | |
|---|---|
| Compound of Example 3 | 2 g |
| 4-[(2-Oxo-3-bornylidene)methyl]phenyl-trimethylammonium methylsulphate | 2 g |
| 50:50 mixture of glycerol monostearate and polyethylene glycol stearate containing 100 moles of ethylene oxide | 8 g |
| Stearyl alcohol | 6 g |
| Benzoate of $C_{12-15}$ alcohols, sold under the name "FINSOLV TN" by FINETEX | 30 g |
| Polydimethylsiloxane sold under the name DOW CORNING FLUID 200 by DOW CORNING | 1 g |
| Tert-butyl-para-cresol | 0.05 g |
| Glycerin | 20 g |
| Ethylenediaminetetraacetic acid potassium salt dihydrate | 0.1 g |
| Preservative | 0.2 g |
| Perfume | 0.2 g |
| Water q.s. | 100 g |

The preparation is similar to that of Example 9, except that the 4-[(2-oxo-3-bornylidene)methyl]phenyl-trimethylammonium methylsulphate is dissolved in the aqueous phase.

Compositions for protection of the hair

EXAMPLE 16

| Gelled lotion | |
|---|---|
| 3-[4-(5-Sulphobenzimidazol-2-yl)benzylidene]-2-bornanone acid | 2.25 g |
| Hydroxyethylcellulose | 0.75 g |
| Propylere glycol | 4.5 g |
| Triethanolamine q.s. pH 8.1 | |
| Water q.s. | 100 g |

EXAMPLE 17

| Rinse in emulsion form | |
|---|---|
| Compound of Example 3: 3-[4-(benzothiazol-2-yl)benzylidene]-2-bornanone | 1 g |
| Cetyl/stearyl alcohol | 2.5 g |
| Benzoate of $C_{12-15}$ alcohols, sold under the name "FINSOLV TN" by FINETEX | 15 g |
| Oxyethylenated cetyl/stearyl alcohol containing 15 moles of ethylene oxide | 2.5 g |
| Water q.s. | 100 g |

The compound of Example 3 can be replaced by the same amount of compound of Example 5.

We claim:

1. A compound of formula:

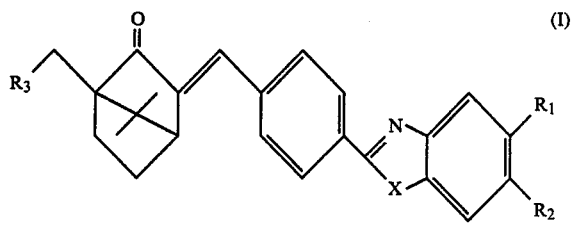

wherein:

X is oxygen, sulphur or an —NR— group, wherein R is hydrogen or a $C_1$–$C_6$ alkyl group;

$R_1$ is hydrogen or a $C_1$–$C_6$ alkyl, a $C_1$–$C_6$ alkoxy, an —$SO_2Cl$ or —$SO_2NR_4R_5$ group wherein $R_4$ and $R_5$, which may be identical or different, are hydrogen, a $C_1$–$C_{12}$ alkyl or $C_2$–$C_4$ hydroxyalkyl group, or $R_1$ is an —$SO_3H$ or —$SO_3^{\ominus}M^{\oplus}$ group wherein M is potassium or sodium or an $N(R_6)^{\oplus}_4$ group, wherein each $R_6$, which may be identical or different, is hydrogen, a $C_1$–$C_6$ alkyl or $C_2$–$C_4$ hydroxyalkyl group;

$R_2$ is hydrogen, a $C_1$–$C_6$ alkyl or $C_1$–$C_6$ alkoxy group, or $R_1$ and $R_2$ together are a methylenedioxy group;

$R_3$ is hydrogen or an —$SO_3H$, —$SO_3^{\ominus}M^{\oplus}$ or —$SO_2NR_4R_5$ group wherein M, $R_4$ and $R_5$, which may be the identical or different to the M, $R_4$ and $R_5$ groups respectively above, have the same meanings as above.

2. A compound according to claim 1 wherein X is oxygen.

3. The compound of claim 2 selected from the group consisting of 3-[4- benzoxazol-2-yl)benzylidene]-2 bornanone and 3-[4-(5-ethylbenzoxazol -2-yl)benzylidene]-2-bornanone.

4. The compound according to claim 1 wherein X is sulphur.

5. 3-[4-benzothiazol-2-yl)benzylidene]-2-bornanone.

6. The compound according to claim 1 wherein X is an —NR— group.

7. The compound according of claim 6 selected from the group consisting of 3-[4-(benzimidazol-2-yl)benzylidene]-2 bornanone, 3-[4-(5-methylbenzimidazol-2-yl)benzylidene]-2-bornanone, 3-[4-(5-methoxybenzimidazol-2-yl)-benzylidene]-2-bornanone, 3-[4-(5-chlorosulphonylbenzimidazol-2-yl)benzylidene]-2-bornanone, 3-[4-(5-sulphobenzimidazol-2-yl)benzylidene]-2-bornanone potassium salt or the corresponding acid and 3-[4-(N-methylbenzimidazol-2-yl) benzylidene]-2-bornanone.

8. A cosmetic composition comprising, as a protective agent against UV-A rays, an effective amount of at least one compound of formula (I) as claimed in claim 1 in a cosmetically acceptable medium.

9. A composition according to claim 8 wherein the compound of formula (I) is present in a proportion of from 0.5 to 10% by weight relative to the total weight of the composition.

10. A composition according to claim 9 wherein the compound of formula (I) is present in a proportion of from 1 to 6%.

11. A composition according to claim 8 which is a solution, lotion, emulsion, gel or solid stick, or is packaged as an aerosol.

12. A composition according to claim 8 which comprises a solubilization solvent, selected from the group consisting of a $C_1$-$C_6$ monohydric alcohol or polyol, glycol or glycol ether, an oil, a wax or a mixture thereof, and a hydroalcoholic solution.

13. A composition according to claim 8 which comprises, at least one cosmetic adjuvant selected from the group consisting of a thickener, a softener, a humectant, an emollient, a wetting agent, a surfactant, a preservative, an antifoam, a perfume, an oil, a wax, a coloring, a pigment and a bactericide.

14. A composition according to claim 8 in the form of a composition protecting against sunlight which additionally comprises at least one water-soluble or lipid-soluble sunscreen agent having a filtering action with respect to UV-B rays.

15. A composition according to claim 14 wherein the water-soluble or lipid soluble sunscreen agent is coffee oil, a camphor derivative, a salicylic acid derivative, a cinnamic acid derivative, a p-aminobenzoic acid derivative or a benzophenone derivative.

16. A composition according to claim 8 which is a light-stable hair-care composition or a make-up product.

17. A composition according to claim 16 wherein the composition is a hair lacquer, a hair setting lotion, a shampoo, a coloring shampoo, a hair dye, a nail varnish, a lipstick, a treatment cream for the epidermis or a make-up foundation.

18. A composition according to claim 8 which is a composition intended to protect the hair from UV-A rays, which is a shampoo, a lotion, a gel or emulsion to be rinsed, a styling or treatment lotion, a lotion for blow-drying or setting, a hair lacquer, or a composition for permanent waving, dyeing or bleaching the hair.

19. A cosmetic process for protecting the human epidermis or the hair against UV-A rays which comprises applying an effective amount of a composition as claimed in claim 8 to the epidermis or hair.

20. A process for protecting a colored cosmetic composition against UV-A rays, which comprises incorporating an effective amount of at least one compound of formula (I) as defined in claim 1 in the composition.

* * * * *